United States Patent [19]
Meltzer

[11] Patent Number: 5,873,394
[45] Date of Patent: Feb. 23, 1999

[54] AUTOMATED SAMPLE PREPARATION WORKSTATION FOR THE VAPOR DIFFUSION METHOD OF CRYSTALLIZATION AND METHOD OF PREPARATION

[75] Inventor: Walter Carl Meltzer, New Milford, Conn.

[73] Assignee: Cyberlab, Inc., Brookfield, Conn.

[21] Appl. No.: 933,430

[22] Filed: Sep. 18, 1997

Related U.S. Application Data

[60] Provisional application No. 60/051,572 Jul. 2, 1997.
[51] Int. Cl.$^6$ ...................................................... B65B 1/04
[52] U.S. Cl. ........................... 141/130; 422/99; 422/100; 436/180; 436/174
[58] Field of Search .............................. 141/130; 422/99, 422/100; 436/180, 174

[56] References Cited

U.S. PATENT DOCUMENTS

4,265,855  5/1981  Mandle et al. ........................... 141/130
5,102,623  4/1992  Yamamoto et al. ..................... 141/130

*Primary Examiner*—Steven O. Douglas
*Attorney, Agent, or Firm*—Hoffman, Wasson & Gitler

[57] ABSTRACT

An automated sample preparation workstation and sample preparation method for the vapor diffusion method of crystallization which performs multiple processing functions such as pipetting, diluting, coverslip manipulations, plate greasing and the like under microprocessor control. The apparatus is responsive to operator-entered processing requests and performs complex and accurate processing functions. The disclosed apparatus is menu-driven and thus easy to learn and simple to operate.

13 Claims, 12 Drawing Sheets

AUTOMATED SAMPLE PREPARATION WORKSTATION FOR THE VAPOR DIFFUSION METHOD OF CRYSTALLIZATION AND METHOD OF PREPARATION

This application claims benefit of Provisional Application No. 60/051,572 filed Jul 2, 1997.

The U.S. Government has a paid-up license in this invention and the right in limited circumstances to require the patent owner to license others on reasonable terms as provied by the terms of Grant No. 1-R43-GM55049-01 awarded by the National Institute of General Medical Sciences.

BACKGROUND OF THE INVENTION

The present invention relates to an automated sample preparation workstation for the vapor diffusion method of crystallization.

In the past, automated sample preparation workstations have been used which process samples using pipetting, diluting, and dispensing techniques to mix and prepare samples. Some automated devices are quite complex, inaccurate, and require many manual steps and much preparation thereby negating the benefits of automating (i.e., the operator must prepare multiple samples before the device is able to process them; the preparation of these samples requires an intimate knowledge of science and mathematics; and, in addition, the operator must possess a detailed knowledge of the steps the system must perform to be able to operate it.) While devices are known which provide fewer processing functions, such devices are inherently limited in their overall capability.

In effect, the art does not, in general, have the capability of performing all the steps required for automating sample preparation for the vapor diffusion method of crystallization using an operator who may not possess the necessary expertise described above to prepare samples. For instance, if an operator desires to prepare a group of samples to be crystallized (usually prepared in a 24-well plate), the equipment typically requires that the operator have considerable background experience in order to achieve the desired results. The equipment cannot communicate, prepare or summarize information on an intelligent level with an operator not having the necessary expertise in order to complete the desired vapor diffusion method of crystallization.

As indicated above, it is most important that all the steps of sample preparation be done accurately, reproducibly, timely and easily. One very apparent difficulty is the very small volumetric ranges which must be handled when preparing samples. Prior equipment has not in general been able to provide such an accurate and precise processing capability with very small volumes while at the same time providing an apparatus which is quite simple and easy to use.

The ability to seal the wells is required in the sample preparation process. Prior equipment, in general, does not address this requirement and the operator must do this manually.

It would be highly desirable to provide an improved automated sample preparation workstation for the vapor diffusion method of crystallization which can accurately and repeatably prepare multiple samples with limited operator intervention. Most particularly, it would be desirable to provide a workstation which could completely automate the process of preparing these samples, including the sealing of wells; the preparation of various solutions in those wells; and the pipetting, diluting and dispensing of solutions, macromolecules or other substances onto coverslips or some other structure which would then be sealed in or on a well.

SUMMARY OF THE INVENTION

It is an object of the present invention to provide an improved device for preparing crystals based on the vapor diffusion method of crystallization.

The workstation includes an XYZ positioning device with several tools mounted on the probe head. The tools include an automated greasing device; two probes for pipetting liquids; and a probe which uses a vacuum line to pick up small coverslips. There are several devices which are part of the layout accessed by the probe head, including a pneumatically operated cover for vials containing solutions so they will not evaporate between pipetting and a device which holds the coverslip after it has been placed there by the vacuum operated probe and allows it to be turned over and then back again. There are also places for multiple plates, disposable pipette tips, and the macromolecules or other substance to be crystallized.

Software provided with the workstation allows for easy operation of the device with minimal knowledge of the scientific specifics required.

Further advantages achieved by the invention will become apparent from the following detailed description when taken in conjunction with the accompanying drawings.

BRIEF DESCRIPTION OF THE DRAWINGS

FIG. 1-A depicts a diagram of a crystallization workstation according to the present invention;

FIG. 1-B depicts additional details of a crystallization workstation according to the present invention;

FIG. 8-A depicts a device used to hold coverslips and turn them upside down so macromolecules or other substances can be placed on the side of the coverslip which has not been contaminated by the bottom of the vacuum operated coverslip rabber probe. The device is displayed with and without a coverslip;

DETAILED DESCRIPTION OF THE DRAWINGS

As described above, the present invention relates to a workstation which automates the process of preparing samples for the vapor diffusion method of crystallization. By way of general overview, the workstation has a deck layout which includes: a rack with an automatic cover containing vials filled with solutions; a vial filled with the substance to be crystallized; plates within which the reaction will take place; disposable pipette tips; a holder for coverslips; and a device for turning the coverslips over to allow pipetting to the other side.

The vapor diffusion method, as indicated by its name, is the diffusion of volatile components from the sample to the bulk reservoir in an isolated environment. There are several types of vapor diffusion methods which can be performed by the workstation; the method described here is called the hanging drop method. A small amount of the substance (A) to be crystallized, usually 1 to 10 ul, is mixed with a chemical or group of chemicals (B). This mixture of A and B is then placed in a sealed container, along with, but not touching a much larger amount of B. If successful, the vapor contained in the sealed container allows A to crystallize. The crystal which is formed can then be analyzed by various methods.

The following discussion of the drawings is in the order of the method of operation.

Figure 1:
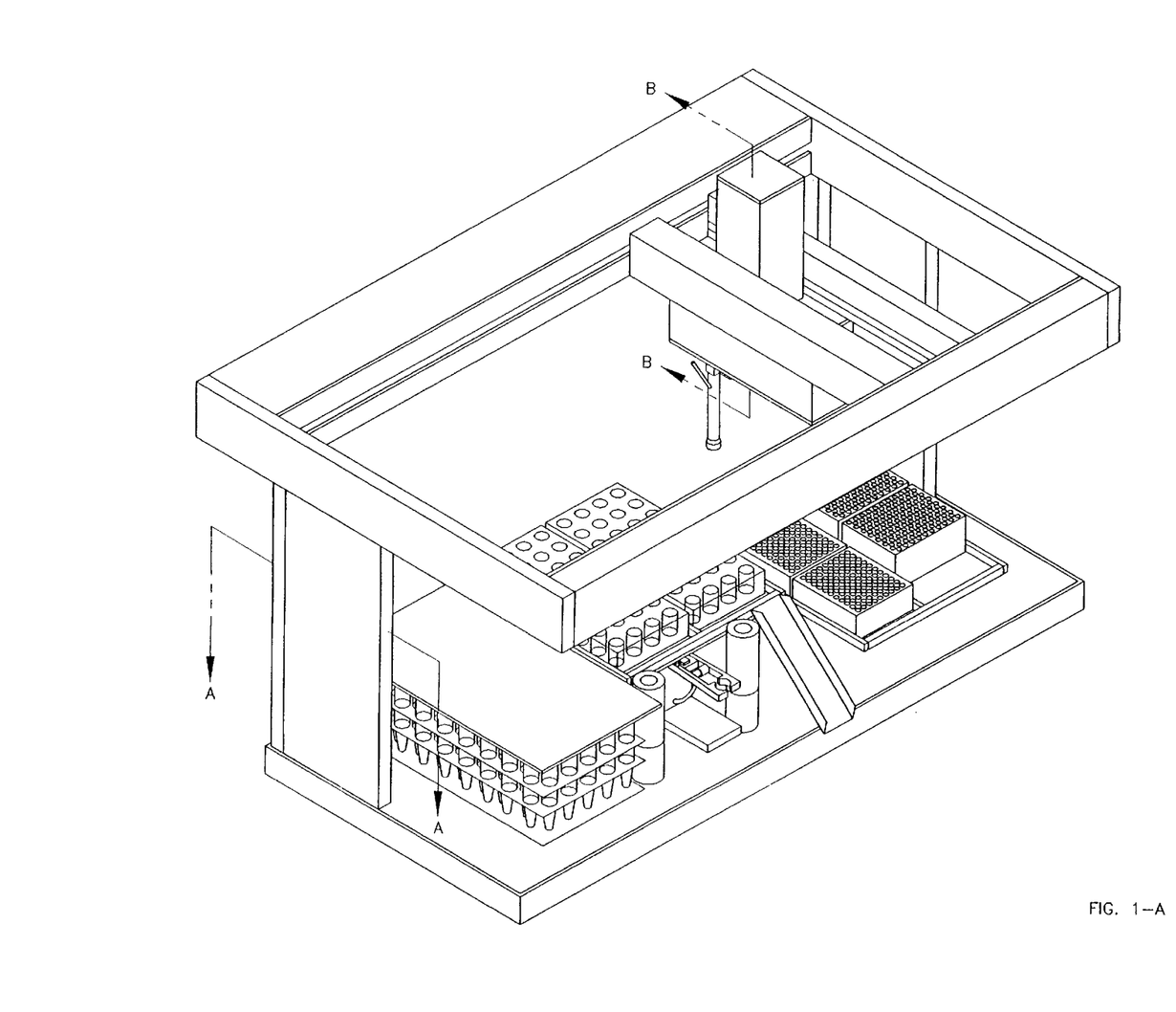

Referring now to FIG. 1-B, a diagram of workstation 1 which automates the process of preparing crystals using the vapor diffusion method is depicted. Layout 1 is made up of two sizes of disposable pipette tips 8 and 8a; container 9 for holding waste solutions; container 10 for holding substance to be crystallized; device 11 for turning the coverslips over; holder 12 for stacking new coverslips; holder 14 for plates; rack 13 for holding chemicals to be mixed with substance from 10; chute 17 for disposing tips; dilutor 16 for pipetting liquids; and device 3 for automatically covering rack 13 chemicals.

Figure 4:
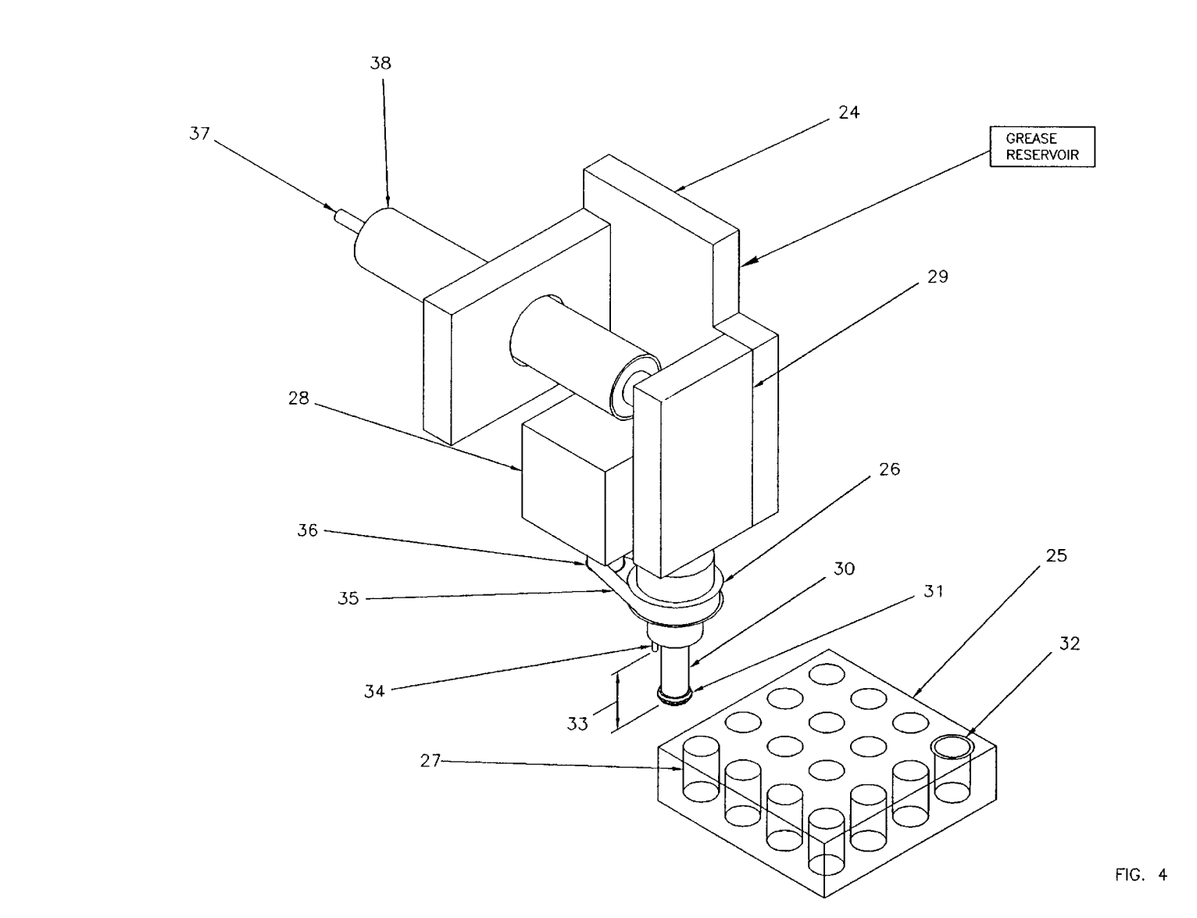
FIG. 4 depicts a diagram of the automated greasing device.
Figure 5:
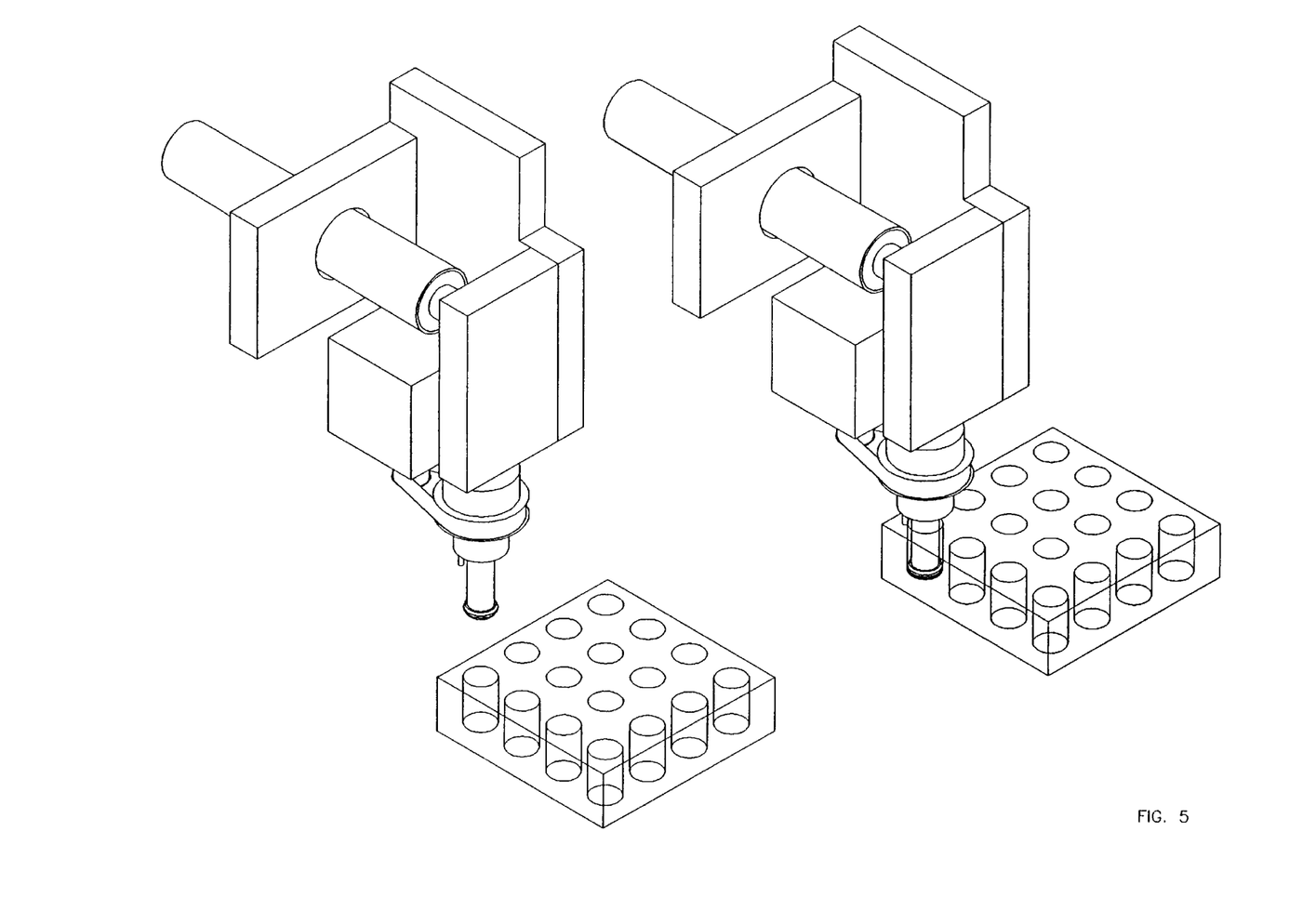
FIG. 5 depicts the automated greaser applying grease to the rim of a well on a plate.
Figure 6:
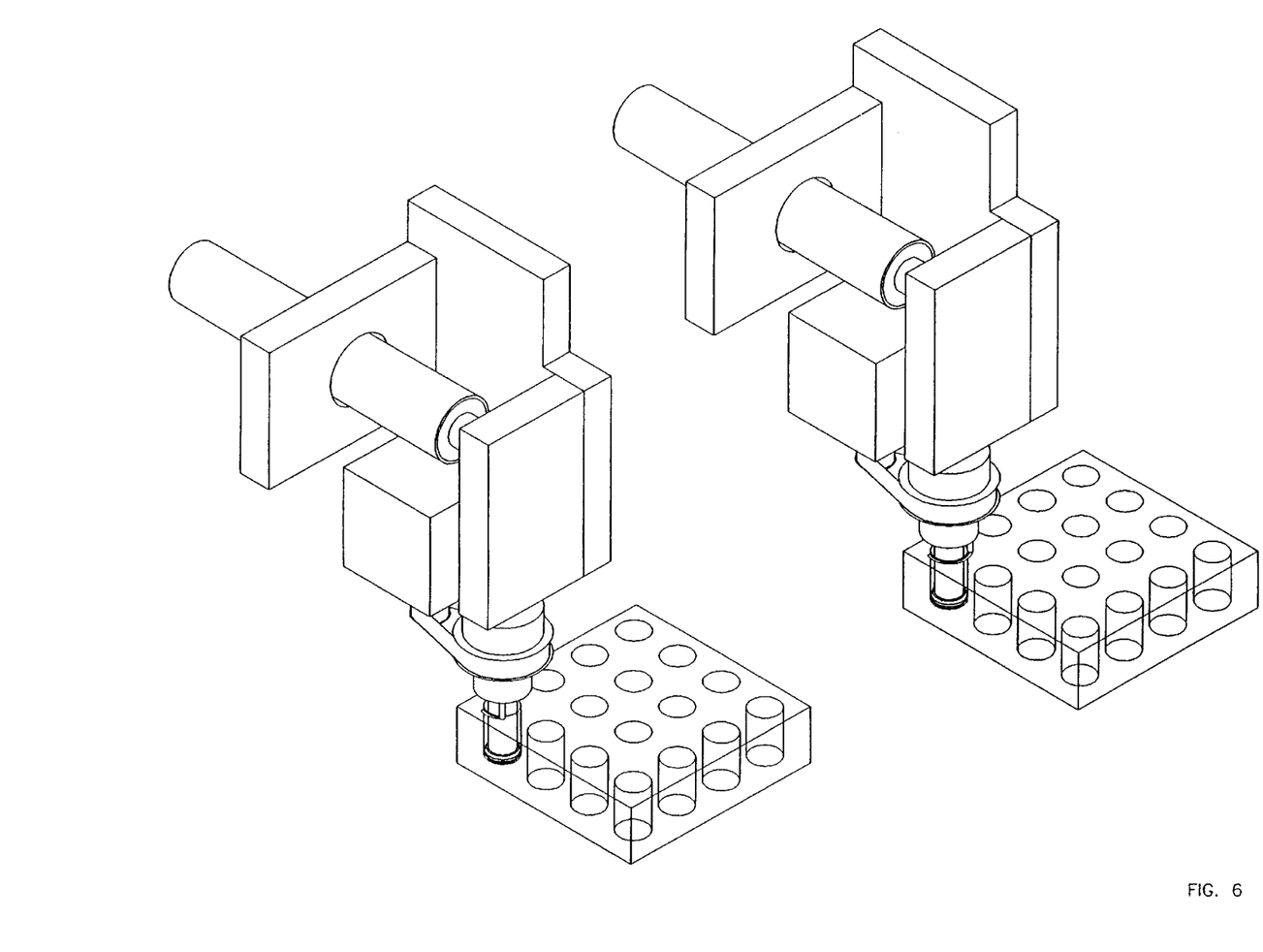
FIG. 6 depicts the continuation of the greaser applying grease to the rim of a well on a plate (see FIG. 5)
Figure 7:
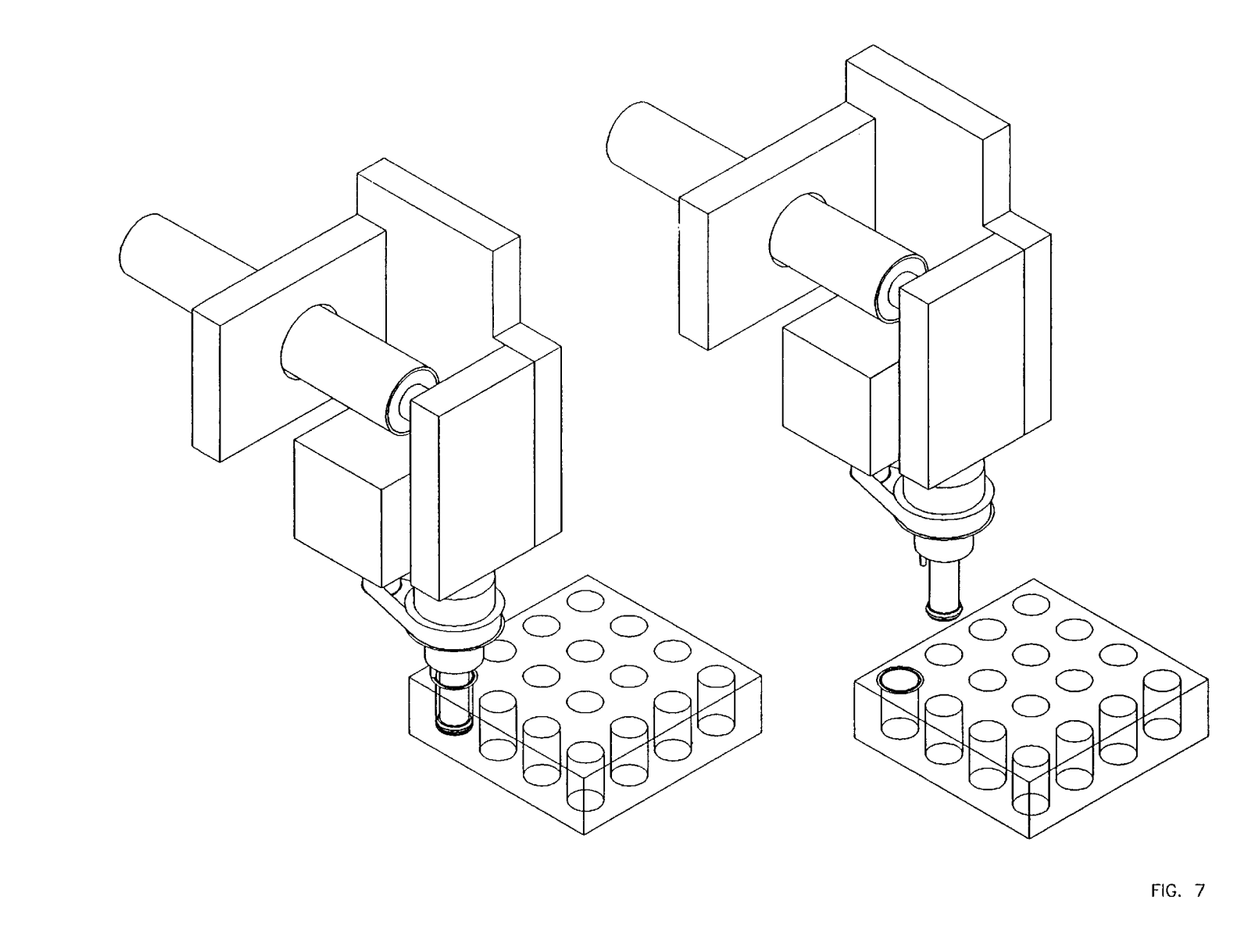
FIG. 7 depicts the end of one cycle of the automated greaser applying grease to the rim of a well on a plate (see FIG. 5 and FIG. 6)

Probe head 2 depicted in FIG. 1-B has multiple tools attached to it. Device 7 is an automatic greaser. It can be seen in FIG. 4 automatically placing a thin bead of grease along rim 32 of well 27 on plate 25. As shown in FIG. 4, the automated greaser uses compressed air 37 to push grease through syringe 38. The grease then travels through a hole in block 29 to applicator head 26 which is being turned by motor 28 which is attached to applicator head 26 by belt 35. The grease is dispensed through nozzle 34 while being positioned by guide 31 at the end of post 30. Measurement 33 is the distance from the bottom of guide 31 to the bottom of nozzle 34. See FIG. 5, FIG. 6 and FIG. 7 for a series of drawings depicting the full cycle of the automated greaser.

Figure 2:
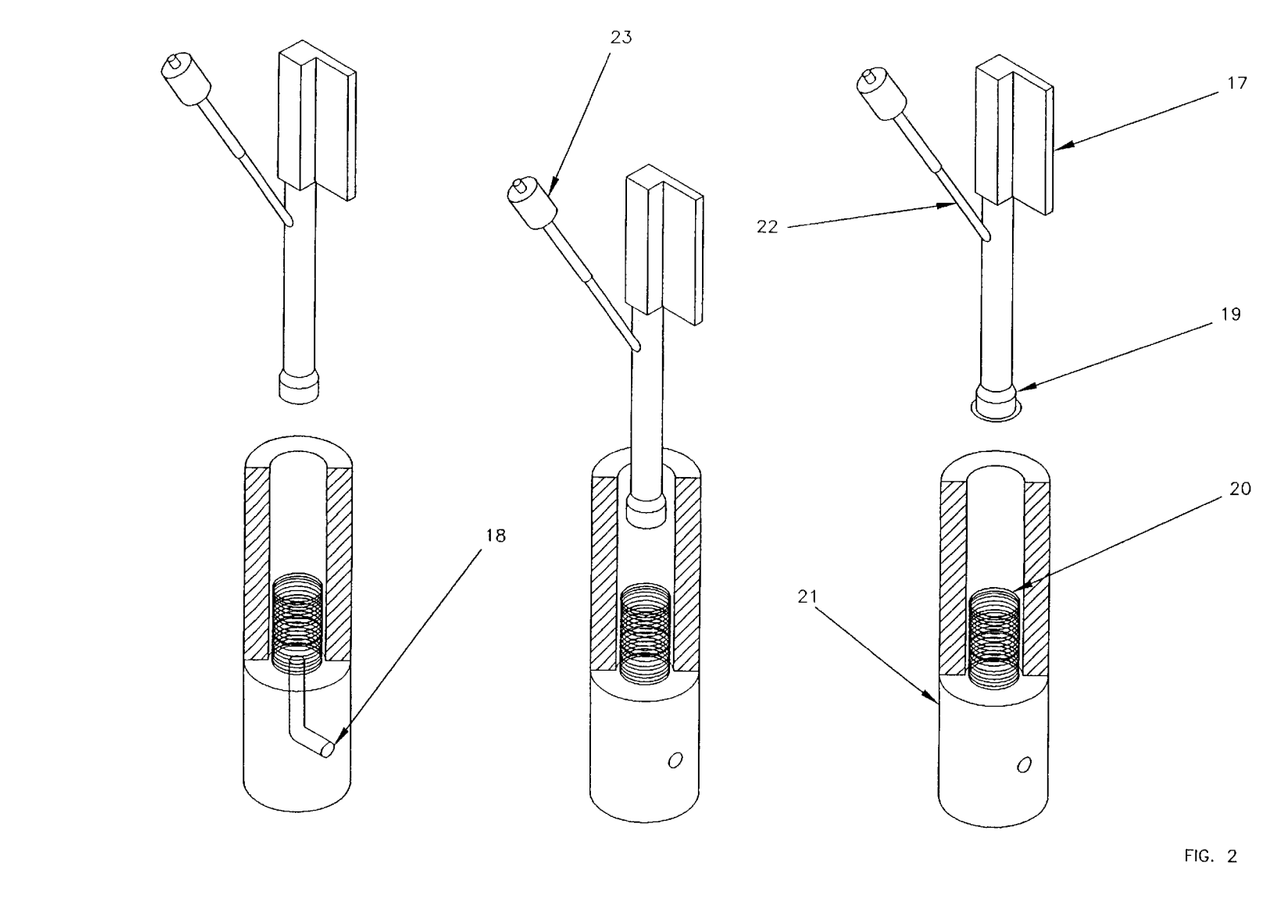
FIG. 2 depicts the vacuum operated coverslip grabber probe completing a cycle of picking up a coverslip from the coverslip holder;.

FIG. 2 depicts a vacuum operated transfer device for picking up coverslips and moving them. The device has: a vacuum hookup 22; a mounting block 17 to allow it to be attached to probe head 2 in FIG. 1-B; and a tip 19 used to grab coverslips. Coverslip holder 21 is shown with relief path 18 which allows the vacuum switch 23 to detect when the coverslip holder 21 is empty.

FIG. 1-B also depicts two pipetting probes 5 and 6. One of these probes is fitted with a nozzle which can pickup a small disposable pipette tip (1 to 10 ul) and the other probe is fitted with a nozzle which can pick up a large disposable pipette tip (200 to 1,000 ul). Probes 5 and 6 are used to pipette liquids into the wells and onto one side of the coverslips. The disposable tips help prevent contamination.

Figure 3:
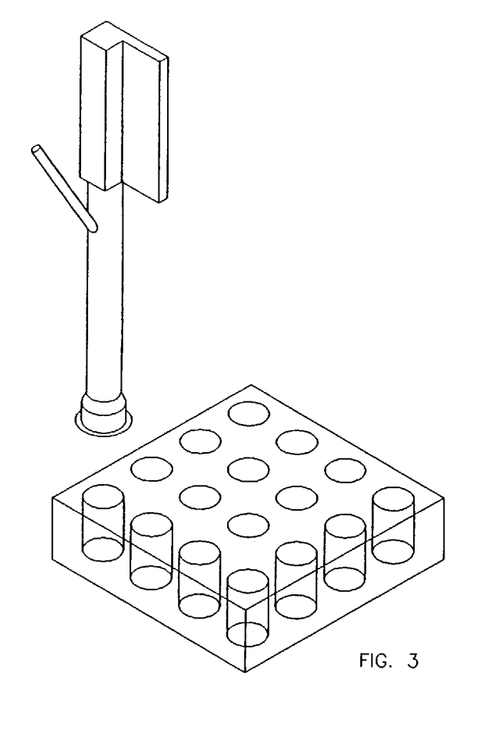
FIG. 3 depicts the vacuum operated coverslip grabber probe of FIG. 2 removing a coverslip from the coverslip turning device of FIG. 8-A and placing the coverslip onto the previously greased rim of a multi-well plate of FIG. 4.
Figure 8:
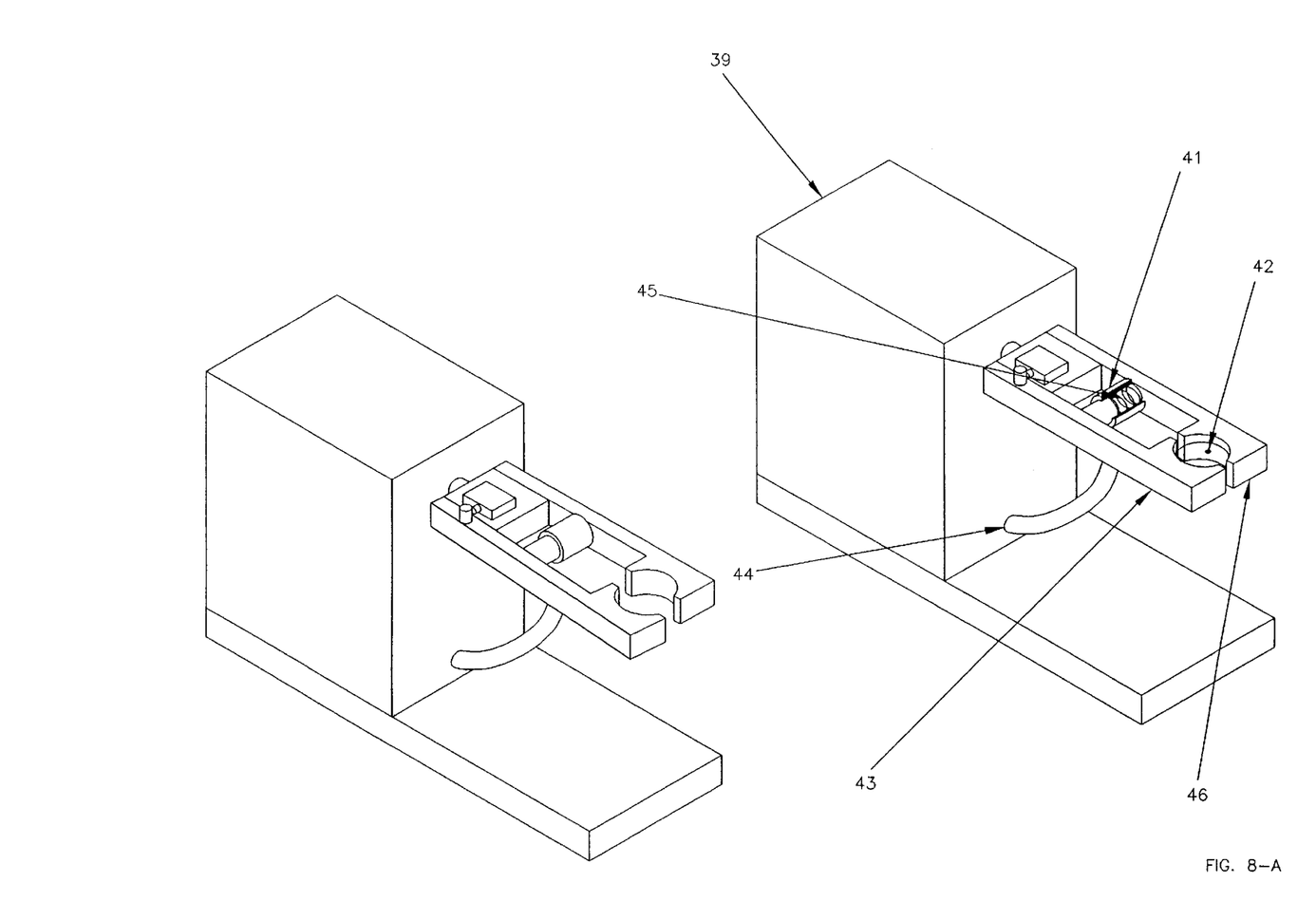
Figure 9:
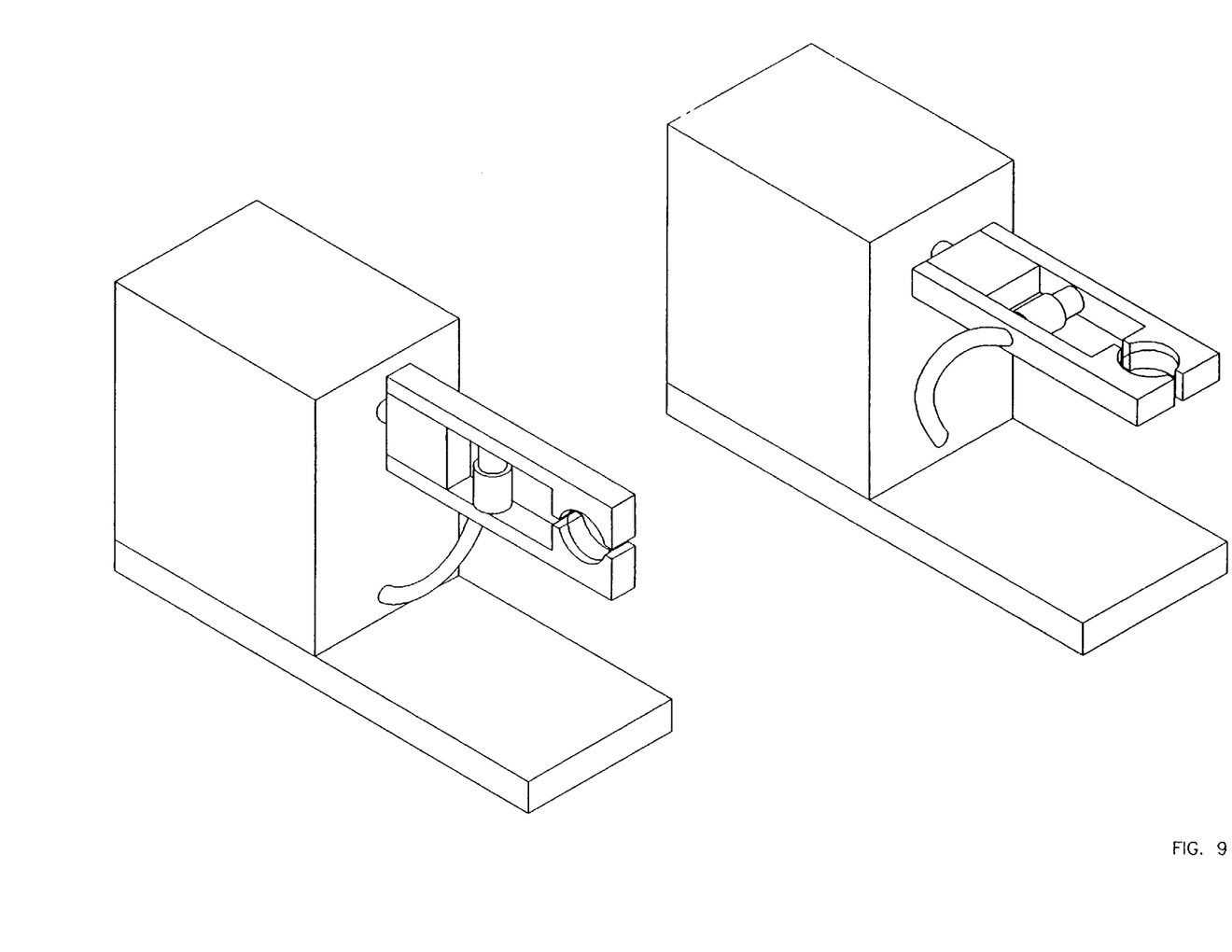
FIG. 9 depicts the continuation of the operation of the device used to hold and turn coverslips in FIG. 8.

FIG. 8-A depicts a coverslip manipulating device which holds coverslips and turns them over and back again. Specifically, the coverslip is placed between arms 46 and 43 by the vacuum operated device for picking up coverslips depicted in FIG. 3. Arm 43 is pulled toward arm 46 by applying a vacuum to cylinder 41. There is a slight gap between the plunger and the cylinder surrounding it which provides an escape for some of the air pressure. The vacuum remaining applies a gentle pressure to the edge of the coverslip, allowing it to be held firmly in position. FIG. 8-A, FIG. 9 and FIG. 3 show the entire sequence of the coverslip manipulating device. As can be seen in the figures, the arms 46 and 43 are connected to a cylinder. The cylinder is rotated by any conventional rotational means as, for example, a motor housed within a tower 39.

Figure 10:
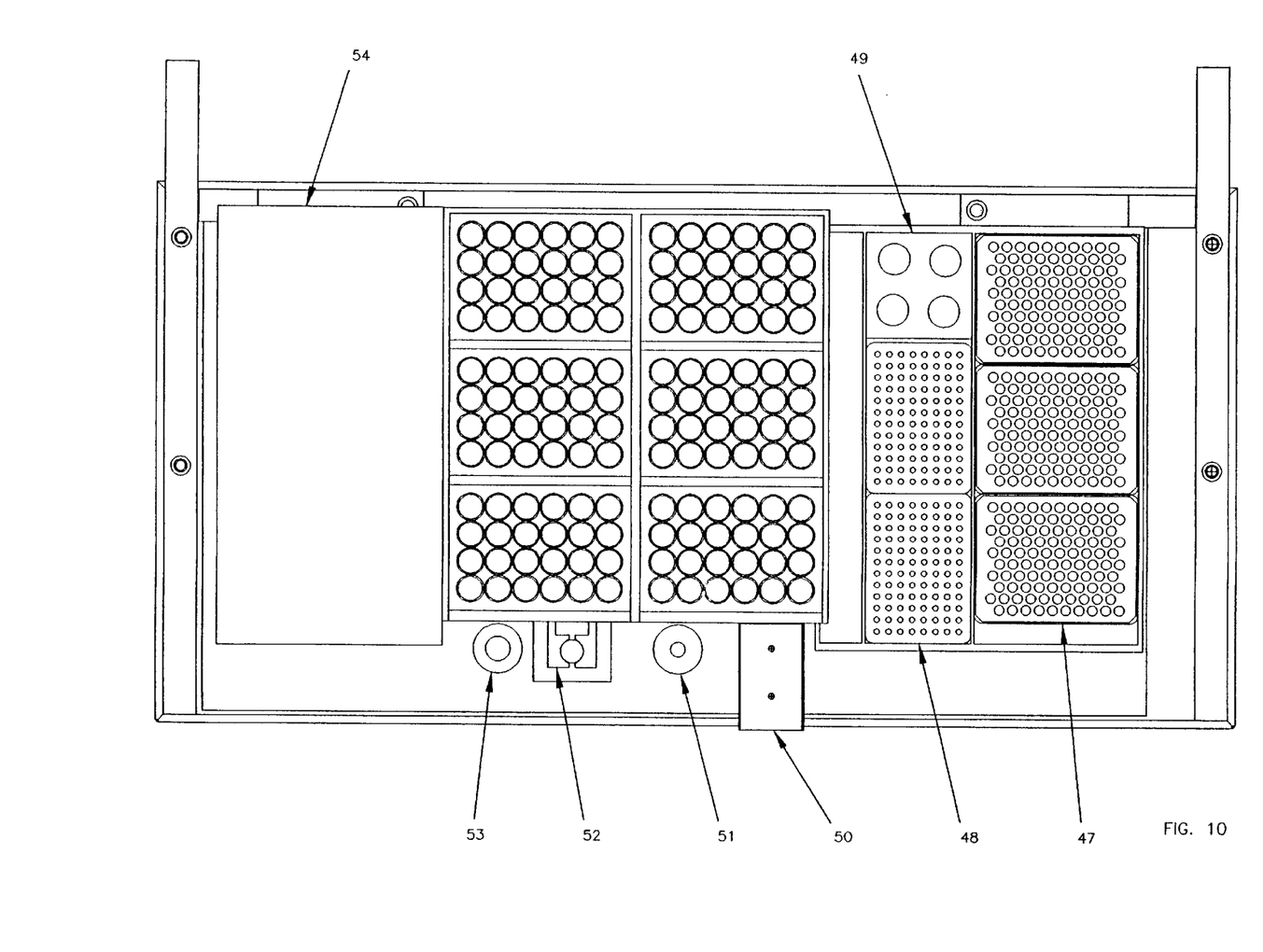
FIG. 10 depicts the workstation layout with the vial cover closed over the vials (54)
Figure 11:
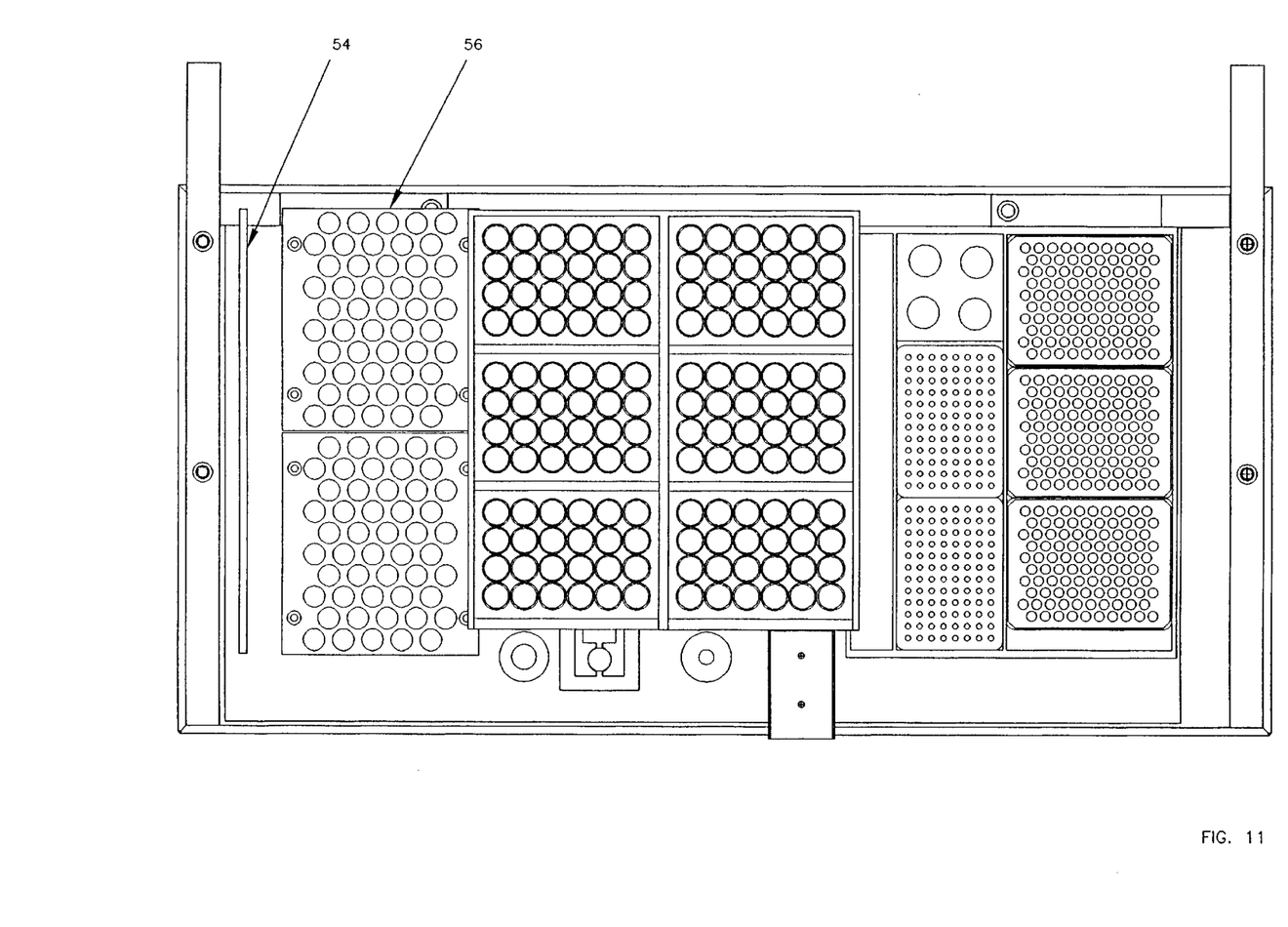
FIG. 11 depicts the workstation layout with the cover open revealing the vials (56).

FIG. 10 depicts the physical layout of the workstation in detail with vial cover lid 54 in the closed position. FIG. 11 depicts the same layout but with the vial cover lid 54 open. This is another view of the layout as described above in FIG. 1-A and FIG. 1-B.

A typical method of operation using the present invention to prepare samples using the hanging drop vapor diffusion method would be as follows:

1. A user would make sure sufficient quantities of the following were loaded onto the workstation: disposable tips, trays, solutions, empty waste container, coverslips and a grease cartridge;

2. The user would start the workstation using the software provided;

3. The automatic greaser would apply grease to each well of a plate;

4. The tubing connecting the large pipetting probe to the dilutor is primed, usually with water, and the large pipetting probe picks up a new disposable tip (usually a 1 ml tip);

5. Using the large pipetting probe, solutions are transferred from a rack of vials to wells on a plate;

6. The coverslip transfer device transfers a coverslip from the coverslip holder to the coverslip manipulator;

7. The coverslip manipulator turns the coverslip over;

8. The tubing connecting the small pipetting probe to the dilutor is primed, usually with water, and the small pipetting probe picks up a new disposable tip (usually a 1–10 ul tip);

9. The small pipetting probe aspirates a small amount (1 to 10 ul's) of the compound to be crystallized from a vial and dispenses it onto the coverslip;

10. The small pipetting probe aspirates a small amount (1 to 10 ul's) from the well containing the mixing compound and places it onto the coverslip with the compound to be crystallized and mixes it;

11. The coverslip manipulator turns the coverslip over again with the drop of the mixed solutions now hanging upside down on the underside of the coverslip; and 12. The coverslip transfer device picks up the coverslip and places it on top of the rim of a greased well with sufficient pressure to seal the well from the outside environment.

It should be clear that the aspects of the present invention have many applications and are not limited to the hanging drop method of vapor diffusion crystallization.

What is claimed is:

1. An automated sample preparation workstation comprising:

a rack adapted for vials filled with solutions to be screened;

a plate within which said solutions will be placed for a reaction to take place;

an automated greaser for applying a layer of grease to an edge of a well on said plate;

a coverslip which is placed on said well by an automated coverslip transfer device mounted on an automated probe to seal said well from an outside environment; and an automated fluid pipetting system mounted on said probe which can pipette liquids to positions on said workstation.

2. An automated sample preparation workstation as claimed in claim 1, wherein said automated coverslip transfer device is computer controlled.

3. An automated sample preparation workstation as claimed in claim 1, wherein said automated coverslip transfer device is vacuum operated and comprises a vacuum hookup, a mounting block for attachment to said probe head, and a tip used to grab coverslips.

4. An automated sample preparation workstation as claimed in claim 1, further comprising a device for holding a plurality of coverslips.

5. An automated sample preparation workstation as claimed in claim 1, further comprising a cover for said vials.

6. An automated sample preparation workstation as claimed in claim 5, wherein said cover is pneumatically operated.

7. An automated sample preparation workstation as claimed in claim 1, further comprising a device for holding a plurality of plates.

8. An automated sample preparation workstation as claimed in claim 1, further comprising disposable pipette tips for use with said automated pipetting system.

9. An automated sample preparation workstation as claimed in claim 8, further comprising a multipositionable rack for holding said disposable pipette tips.

10. An automated sample preparation workstation as claimed in claim 1, further comprising a waste container for holding waste solutions.

11. An automated sample preparation workstation as claimed in claim 1, wherein said automated probe has said automated greaser and said automated pipetting system attached thereon, and is movable in all planes.

12. An automated sample preparation workstation as claimed in claim 1, wherein said automated greaser comprises: a syringe; a grease reservoir; and a compressed air source, to push said grease through said syringe; a block for transferring said grease from said syringe to an applicator head; and a nozzle located on said applicator head for dispensing said grease onto said edge of said well.

13. A method of preparing a sample for vapor diffusion crystallization using said workstation as claimed in claim 1, comprising the steps of:

applying said layer of grease to said edge of said well on said plate;

pipetting solutions from said vials to said plate;

transferring said coverslip from a coverslip holder to said coverslip transfer device;

turning said coverslip over;

dispensing a small amount of a compound to be crystallized from said vials and dispensing said compound onto said coverslip;

turning said coverslip over again to allow said coverslip to be picked up by said automated coverslip transfer device; and sealing said coverslip on said well which has been greased to seal same from said outside environment.

* * * * *